(12) United States Patent
Kisker et al.

(10) Patent No.: US 8,321,021 B2
(45) Date of Patent: Nov. 27, 2012

(54) STIMULATION SYSTEM, IN PARTICULAR A CARDIAC PACEMAKER

(75) Inventors: Erhard Kisker, Dusseldorf (DE); Heinrich Wieneke, Essen (DE)

(73) Assignee: Universität Duisburg-Essen, Essen (DE)

(*) Notice: Subject to any disclaimer, the term of this patent is extended or adjusted under 35 U.S.C. 154(b) by 1082 days.

(21) Appl. No.: 12/171,955

(22) Filed: Jul. 11, 2008

(65) Prior Publication Data

US 2009/0024180 A1  Jan. 22, 2009

Related U.S. Application Data

(63) Continuation-in-part of application No. PCT/EP2006/012193, filed on Dec. 18, 2006.

(30) Foreign Application Priority Data

| Jan. 13, 2006 | (DE) | 10 2006 001 968 |
| Feb. 17, 2006 | (DE) | 10 2006 007 403 |
| Sep. 8, 2006 | (DE) | 10 2006 042 850 |

(51) Int. Cl.
 *A61N 1/365* (2006.01)

(52) U.S. Cl. .................. 607/32; 607/2; 607/9

(58) Field of Classification Search .......... 607/2, 9, 607/32, 33, 37, 126
See application file for complete search history.

(56) References Cited

U.S. PATENT DOCUMENTS

| 3,820,090 | A | 6/1974 | Wiegand |
| 4,275,739 | A | 6/1981 | Fischell |
| 4,857,822 | A | 8/1989 | Tabisz et al. |
| 4,950,550 | A | 8/1990 | Radeloff et al. |
| 5,170,784 | A | 12/1992 | Ramon et al. |
| 5,405,367 | A | 4/1995 | Schulman et al. |
| 5,411,535 | A * | 5/1995 | Fujii et al. .............. 607/32 |
| 5,573,939 | A | 11/1996 | B.ang.vik et al. |
| 5,584,870 | A * | 12/1996 | Single et al. ............ 607/63 |
| 5,769,877 | A | 6/1998 | Barreras, Sr. |
| 5,782,880 | A | 7/1998 | Lahtinen et al. |
| 5,814,089 | A * | 9/1998 | Stokes et al. ............ 607/32 |
| 6,084,792 | A | 7/2000 | Chen et al. |
| 6,164,284 | A * | 12/2000 | Schulman et al. ........ 128/899 |
| 6,191,687 | B1 * | 2/2001 | Dlugos et al. ............ 340/506 |
| 6,208,894 | B1 * | 3/2001 | Schulman et al. ......... 607/2 |
| 2005/0096702 | A1 * | 5/2005 | Denker et al. ............ 607/9 |

(Continued)

FOREIGN PATENT DOCUMENTS

JP  06 079 005  3/1994

(Continued)

OTHER PUBLICATIONS

Abrams, et al., "A Surgical Approach to the Management of Heart-Block Using an Inductive Coupled Artificial Cardiac Pacemaker", The Lancet, Jun. 25, 1960, pp. 1372-1374.

(Continued)

*Primary Examiner* — Carl H. Layno
*Assistant Examiner* — Jon-Eric C. Morales
(74) *Attorney, Agent, or Firm* — Jason H. Vick; Sheridan Ross, PC

(57) ABSTRACT

A stimulation system, an implantable electrode device and a method for operating an implantable electrode device are proposed. A simplified implantation, a simple construction and reliable control are made possible by the electrode device being supplied with energy, and controlled, in an exclusively wireless manner via a time-variable magnetic field. The magnetic field is generated by an implanted control device.

57 Claims, 10 Drawing Sheets

U.S. PATENT DOCUMENTS

| | | |
|---|---|---|
| 2006/0085041 A1 | 4/2006 | Hastings et al. |
| 2007/0088398 A1 | 4/2007 | Jacobson |
| 2007/0150009 A1 | 6/2007 | Kveen et al. |
| 2008/0183247 A1 | 7/2008 | Harding |
| 2009/0018599 A1 | 1/2009 | Hastings et al. |
| 2009/0182426 A1 | 7/2009 | Von Arx et al. |
| 2009/0192381 A1 | 7/2009 | Brockway et al. |
| 2009/0204170 A1 | 8/2009 | Hastings et al. |

FOREIGN PATENT DOCUMENTS

| | | |
|---|---|---|
| WO | WO 98/26840 | 6/1998 |
| WO | WO 98/43700 | 10/1998 |
| WO | WO 00/17997 | 3/2000 |
| WO | WO 01/36014 | 5/2001 |
| WO | WO 2005/042083 | 5/2005 |
| WO | WO 2006/045075 | 4/2006 |
| WO | WO 2008/034005 | 3/2008 |
| WO | WO 2008/139384 | 11/2008 |
| WO | WO 2009/007861 | 1/2009 |

OTHER PUBLICATIONS

Matsushita, et al., "Power Generating Device Using Compound Magnetic Wire", Journal of Applied Physics, May 1, 2000, pp. 6307-6309, vol. 87, No. 9.

Vásquez, et al., "A Soft magnetic Wire for Sensor Applications", Journal of physics D: Applied physics, 1996, pp. 939-949, vol. 29.

Written Opinion for International (PCT) Patent Application No. PCT/EP2006/-12193, (English Translation).

International Preliminary Examination Report for International (PCT) Patent Application No. PCT/EP2006/-12193, issued Sep. 2, 2008.

Official Office Action from German Patent Office for 101 12 329.9-09, May 6, 2008, pp. 1-2.

* cited by examiner

STIMULATION SYSTEM, IN PARTICULAR A CARDIAC PACEMAKER

CROSS-REFERENCE TO RELATED APPLICATION

This application is U.S. CIP National Application under 35 U.S.C. 111(a) and claims priority to PCT Application WO/2007/087875 (PCT/EP2006/012193), filed Dec. 18, 2006, which claims priority to German Applications, 10 2006 001 968.7, filed 13 Jan., 2006, 10 2006 007 403.3, filed 17 Feb., 2006 and 10 2006 042 850.1, filed Aug. 09, 2006, all of which are incorporated herein by reference in their entirety.

An exemplary embodiment of the present invention relates to a stimulation system, in particular for a cardiac pacemaker, an implantable electrode device or stimulation device for a stimulation system as well as a method for operating an implantable electrode device or stimulation device, in particular a cardiac pacemaker.

In the following description of the invention, the focus is primarily on a cardiac pacemaker. However, the present invention is not restricted to this particular solution, but in general can be applied to other stimulation devices which operate electrically and in particular deliver electrical impulses for stimulation.

BACKGROUND OF THE INVENTION

Cardiac pacemakers stimulate the heart beat by means of electrical impulses which are introduced into the muscle tissue of the heart. For this purpose, a cardiac pacemaker is usually implanted, for example, near the shoulder of the thoracic cage, at least one probe or electrical lead being guided from the implanted cardiac pacemaker via a vein into the atrium or the chambers of the heart and anchored there. The electrical lead is problematical or disadvantageous. This runs over a length of about 30 cm in the blood circulation system and can thereby cause undesirable or even fatal physical reactions. Furthermore, the risk of failure of the probes or leads due to material fatigue as a result of the severe mechanical stressing during body movements is particularly high. Another complication frequently encountered is dislocation of the probes triggered by movements of the patient.

Stimulation by magnetic impulses has been proposed, for example, in U.S. Pat. No. 5,170,784 A in order to avoid the electrical lead and the electrode. However, purely magnetic stimulation does not function satisfactorily so that magnetically stimulating cardiac pacemakers have not been generally accepted.

U.S. Pat. No. 5,411,535 A discloses a cardiac pacemaker with an implantable control device and a separate electrode device. Electrical signals of 10 MHz to a few GHz in particular are transmitted without wires between the control device and the electrode device for controlling the electrode device. The actual power supply of the electrode device is provided via a battery integrated in the electrode device. Such cardiac pacemakers with a separate electrode device have not been widely accepted so far. This may be because the electrode device is of a considerable size and has a limited operating time because of the battery.

The article "A Surgical Approach to the Management of Heart-Block Using an Inductive Coupled Artificial Cardiac Pacemaker" by L. D. Abrams et. al., published in the journal "The Lancet", 25 Jun. 1960, pages 1372 to 1374, describes a method for stimulating a heart where an external control device comprising a coil to be located externally on the body is inductively coupled to a coil implanted between the skin and the ribs. Two electrical leads led from the implanted coil to two electrodes in the heart muscle. Apart from the fact that an external control device is generally problematical and not desirable, the wiring between the implanted coil and the electrodes at a distance therefrom results in the same problems as in the usual cardiac pacemaker described above where at least one electrode is connected to the implanted cardiac pacemaker via an electrical lead through a vein. Furthermore, the implantation of a pacemaker system requires opening the thoracic cage and involves an open-heart operation. Moreover, the implanted coil is very sensitive to external electromagnetic fields so that undesirable interfering voltages are induced and appear at the electrodes.

JP 06 079 005 A discloses an implantable cardiac pacemaker whose battery can be inductively recharged from outside via a coil.

U.S. Pat. No. 5,405,367 A discloses an implantable microstimulator. The microstimulator comprises a receiving coil, an integrated circuit and electrodes. It can be supplied with energy and with control information via an external magnetic field generated by an external coil having an allocated oscillator and an allocated stimulation control device. Such a microstimulator is not suitable for cardiac stimulator or as a cardiac pacemaker since it is relatively large for sufficient capacity and requires an external energy supply.

WO 2006/045075 A1 relates to various configurations of systems that employ leadless electrodes to provide pacing therapy. In particular, a single magnetic pulse is used to generate an electrical pulse in an electrode device. This is problematic, in particular due to magnetic saturation.

SUMMARY OF THE INVENTION

One exemplary aspect of the present invention to provide a stimulation system such as a cardiac pacemaker, an implantable electrode device or stimulation device for a stimulation system as well as a method for operating an implantable electrode device or stimulation device, wherein in particular an electrical lead to the electrode device is not required in the implanted state, wherein the electrode device can have a simple and compact structure and/or wherein an energy supply and/or control insensitive to external influences can be achieved.

The above aspect is achieved by a stimulation system according to claim 1, an electrode device according to claim 8, a stimulating device according to claim 16 and a method according to claim 19 or 23. Advantageous further developments are the subject matter of the dependent claims.

Another aspect of the present invention resides in the fact that the implantable electrode device for generating electrical impulses can be supplied with energy and/or preferably directly controlled in an exclusively wireless or leadless manner by means of a time-varying magnetic field. This permits a very simple and compact structure of the electrode device, whereby in particular no wiring of the electrode device is required so that implantation is simplified and the risk of failure of an electrical lead is avoided and in particular, whereby the use of an energy storage device such a rechargeable battery, a battery or similar in the electrode device can be avoided. Furthermore, substantially greater freedom in the placement of the electrode device is obtained.

The magnetic field is preferably generated by an implantable control device so that an external controller can be avoided. This is particularly desirable when the stimulation system is used as a cardiac pacemaker and is substantially more reliable in use than control by an external, i.e. non-implanted, control device.

The electrode device is particularly preferably controlled directly by the time-varying magnetic field. "Direct" control is to be understood in the present patent application in that the electrical impulses are generated in direct dependence on the magnetic field, for example, depending on the magnitude of the magnetic field, the polarity of the magnetic field and/or the rate of change of the magnetic field, particularly preferably without any active electronic component being interposed in the electrode device. Consequently, in the preferred direct control, electrical impulses or stimulations are generated so that they are only temporally correlated to the magnetic field. This also permits a very simple and in particular compact structure of the electrode device and/or a very reliable defined control.

Another aspect of the present invention includes configuring the electrode device such that an electrical impulse is only generated when a minimum field strength of the magnetic field is exceeded. This very simply permits reliable control which in particular is not sensitive to interference when the minimum field strength is selected as suitably high, since strong magnetic fields occur very rarely but alternating electromagnetic fields having various frequencies are very common.

According to one aspect of the present invention, the electrode device must first be activated before a further electrical impulse can be generated. This activation is effected in particular by another signal, preferably by the opposite field direction of the magnetic field, shortly before triggering and generating the next electrical impulse. Thus, two-stage triggering or signal generation is required to generate an electrical impulse by means of the electrode device. This two-stage property results in particularly reliable triggering, i.e., not sensitive to interference.

The aforesaid triggering safety can be further improved or enhanced whereby the activation of the electrode device always takes place shortly before the generation of the next electrical impulse. Accordingly, the possibility that an electrical impulse as a result of an interference signal (external magnetic field with corresponding field orientation and exceeding the minimum field strength) can lead to undesirable or premature triggering of the next electrical impulse is so minimal that there is no risk for a patient.

According to another aspect of the present invention, a coil device having a high number of turns, that is a coil having many turns, is used to generate an electrical impulse having a high voltage of at least 0.5 V, preferably substantially 1 V or more and having a relatively long duration of at least 0.05 to 2 ms. In this case, the coil device can in particular have a soft-magnetic or ultrasoft magnetic core. The high number of turns, in particular at least 1,000 turns, of a suitably insulated wire made of, for example, Cu, Ag or Al in particular having a diameter of about 0.01 to 0.1 mm permits the generation of a strong and long electrical impulse in said sense.

According to a further aspect of the present invention, when the magnetic field is switched on, no continuous or persistent, for example, sawtooth-shaped ascending magnetic field pulse is generated by the control device but a plurality of short magnetic field pulses, in particular so that the core of the coil device or electrode device always varies its magnetization far below the saturation state. Thus, a minimal energy consumption can be achieved, in particular if the largest possible temporal flux variation takes place in the core of the coil device or electrode device throughout the entire duration of the stimulating pulse (optionally a contiguous sequence of electrical impulses of the electrode device; in the present invention, this sequence is considered as a single electrical impulse for stimulation). This can be achieved by short magnetic field pulses.

The magnetic field pulses can be unipolar or bipolar when using soft-magnetic core material. When using bistable materials (in particular Wiegand or pulsed wires), bipolar magnetic fields must be used.

According to an additional further aspect of the present invention, instead of an electrode device, direct electrical stimulation by a magnetisable element can take place. The element in particular comprises a coil core without coil or the like. This means that a coil for transforming the magnetic field into electric current can be omitted. Instead, the magnetisable element generates directly the desired electric impulse for stimulation.

Accordingly, an implantable stimulation device comprises the magnetisable, preferably ferromagnetic element, the magnetization of the element being varied by an external or varying magnetic field so that the magnetic leakage flux of the element results in the desired electrical stimulation or generation of an electrical impulse in the surrounding tissue. This permits a particularly simple structure where electrical contact electrodes are omitted and the associated problems can be avoided.

The proposed electrode device or another electrode device can be used alternatively or additionally to convert the self-action of the heart, in particular a movement of the heart and/or electrical activity of the heart, into a magnetic impulse or another, in particular, electrical signal which can preferably be detected by the stimulation system or another receiving unit.

As has already been explained, the implantable electrode device is used in particular for generating electrical signals to stimulate the heart. However, the present invention is not restricted to this. Rather, the electrode device can generally generate any type of electrical impulse(s) or electrical signals in the human or animal body. The terms "electrode device" and "stimulation system" should accordingly be understood in a very general sense so that other applications and uses, such as for example to influence the brain, can also be understood.

The preceding is a simplified summary of the invention to provide an understanding of some aspects of the invention. This summary is neither an extensive nor exhaustive overview of the invention and its various embodiments. It is intended neither to identify key or critical elements of the invention nor to delineate the scope of the invention but to present selected concepts of the invention in a simplified form as an introduction to the more detailed description presented below. As will be appreciated, other embodiments of the invention are possible utilizing, alone or in combination, one or more of the features set forth above or described in detail below.

Further advantages, properties, features and aspects of the present invention are obtained from the following description of preferred exemplary embodiments with reference to the drawings.

DETAILED DESCRIPTION OF THE INVENTION

Figure 1:
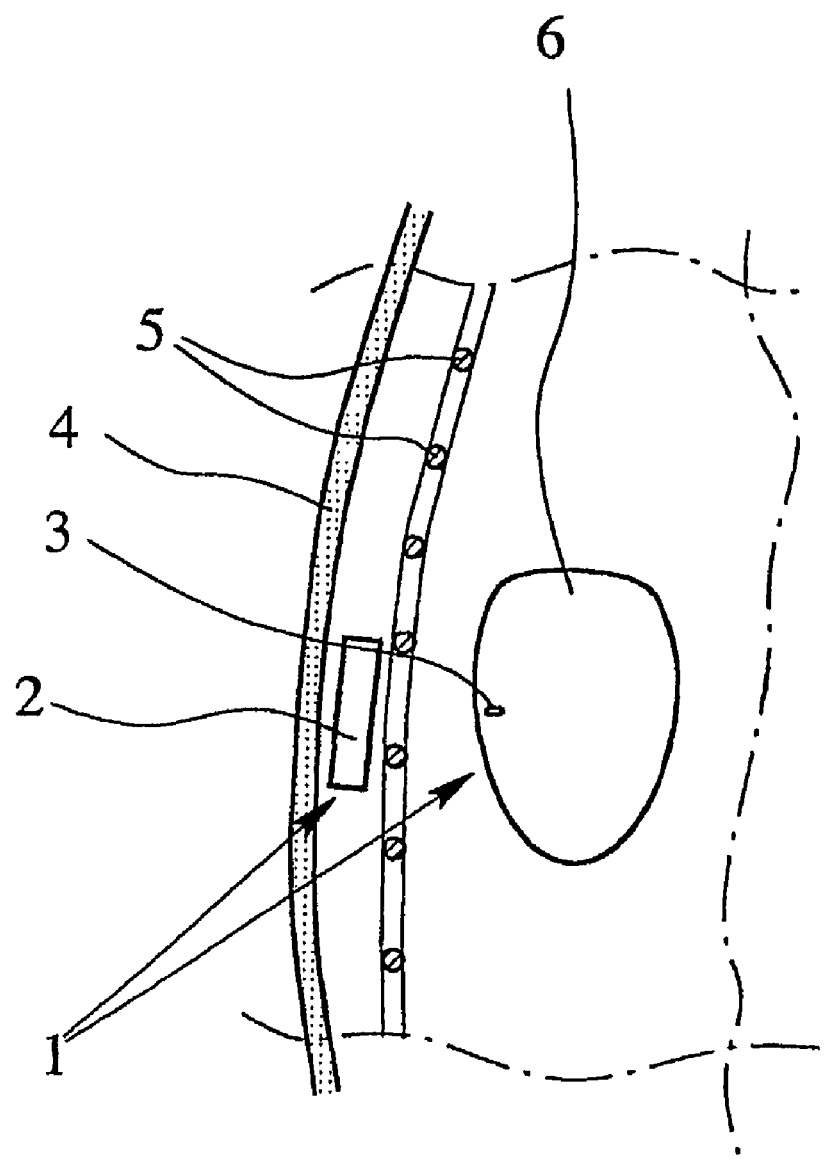
FIG. 1 is a schematic diagram of a proposed stimulation system comprising a control device and an electrode device in the implanted state according to this invention.

In the figures the same reference numerals are used for the same parts or parts of the same type, components and the like, where corresponding or similar advantages and properties are obtained even if a repeated description is omitted.

FIG. 1 is a schematic sectional view of a proposed stimulation system 1 which is in particular configured as or works as a cardiac pacemaker in the example shown. However, the present invention is not restricted to this. For example, the stimulation system 1 can additionally or alternatively operate as a defibrillator or be used for other purposes and at other locations in the human or animal body.

The stimulation system 1 preferably comprises an implantable control device 2 and an implantable electrode device 3 separate therefrom. In the example shown, the control device 2 is implanted, in particular in the thoracic cage between the skin 4 and the ribs 5.

The control device 2 can be implanted as in present-day cardiac pacemakers. However, it is not absolutely essential to implant the control device 2. In principle, the control device 2 can also be used in the non-implanted state, that is, as an external device for controlling the electrode device 3.

Depending on the configuration, the electrode device 3 can also be used independently of the control device 2. For example, it is possible in principle that the electrode device 3 can be supplied with energy and/or controlled by another device, optionally even by a nuclear spin tomograph or the like, with suitable matching. Thus, further possible uses are obtained which go substantially beyond the possible uses of conventional cardiac pacemakers or other stimulation systems.

The electrode device 3 is preferably implanted in the heart 6 or the heart muscle of the patient, who is shown only schematically and in part. The electrode device 3 can be implanted, for example, as described in U.S. Pat. No. 5,411,535 A.

Figure 2:
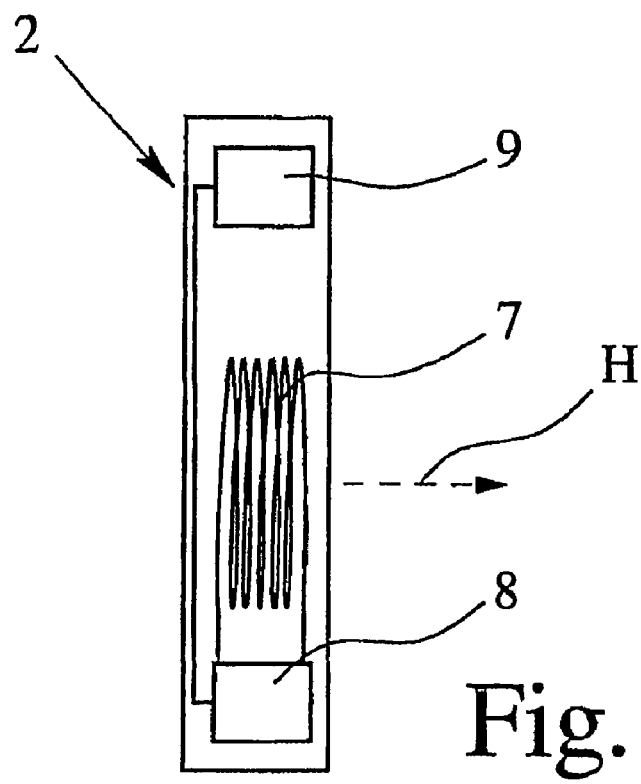
FIG. 2 is a schematic view of the control device according to this invention.

FIG. 2 is a schematic sectional view of the control device 2. In the example shown the control device 2 comprises a coil 7 for generating a magnetic field H, a control 8 and preferably an energy storage device 9 such as a rechargeable battery. The coil 7 can optionally be provided with a ferromagnetic, soft-magnetic or ultrasoft magnetic core or a half-sided cladding or another shoe or conducting element to concentrate the magnetic flux.

The control device 2 or control 8 can preferably receive or take up the required heart information via means not shown and/or via the coil 7 so that the generation of electrical impulses by the electrode device 3 to stimulate the heart 6 can be controlled in the desired manner. For example, reference is also made here to U.S. Pat. No. 5,411,535 A. For example, electrodes, not shown, can also be connected directly to the control device 2, in particular to detect ECG signals or the like.

If necessary, the control device 2 or its energy storage device 9 can be inductively recharged in the implanted state. Thus, in particular when the energy consumption is high, an otherwise necessary operation to change the battery or changing the control device 2 can be avoided. The coil 7 provides a way to generate the magnetic field H, and is preferably used for the inductive charging. However, another induction device not shown can also be used for charging.

Figure 3:
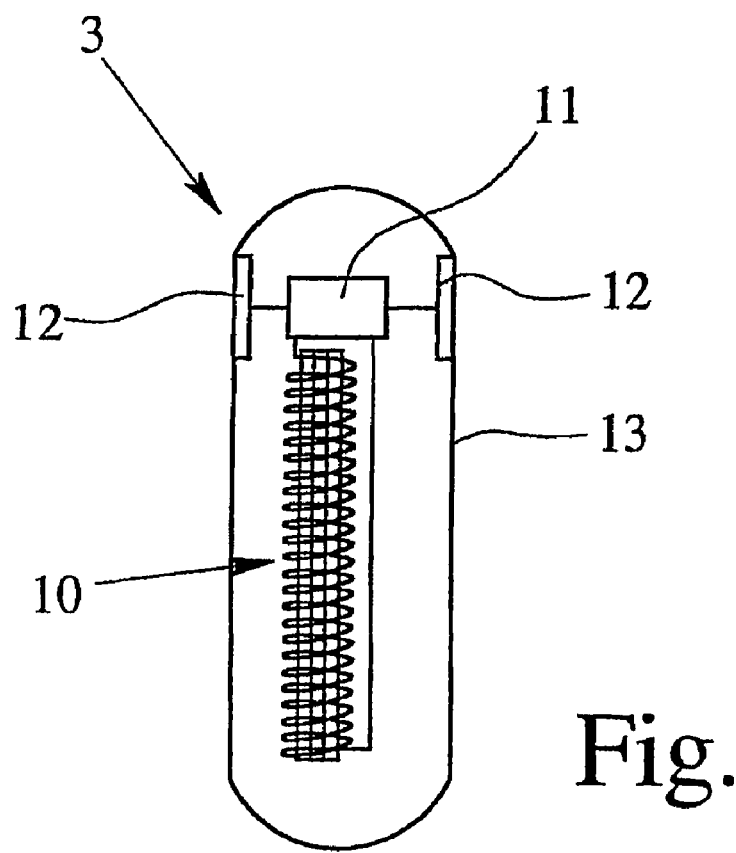
FIG. 3 is a schematic view of the electrode device according to this invention.

FIG. 3 shows the proposed electrode device 3 in a schematic sectional view. The electrode device 3 is preferably constructed only of passive structural elements and/or without an energy storage device such as a battery. In the example shown, this preferably comprises a coil device 10, an optional pulse forming device 11 and preferably at least one electrode 12, preferably at least two electrodes 12, as well as preferably a common housing 13. The components and electrodes 12 are preferably integrated in the electrically insulated housing 13 or attached thereon.

The electrode device 3 is very compact and in particular is configured as substantially rod-shaped or cylindrical. In the example shown, the length is 10 to 20 mm, in particular substantially 15 mm or less. The diameter is preferably at most 5 mm, in particular substantially 4 mm or less. A retaining device can be attached to the electrode device 3, preferably an anchor or a screw which allows the electrode device 3 to be anchored in the heart muscle.

The electrode device 3 is configured to generate electrical impulses for the desired stimulation or signal generation. The electrical impulses are delivered, for example, via the electrodes 12. In the example shown, the electrodes 12 are located on opposite sides. However, the electrodes 12 can also be arranged concentrically or otherwise, for example, at one end or at the opposite ends of the electrode device 3 or the housing 13.

Figure 4:
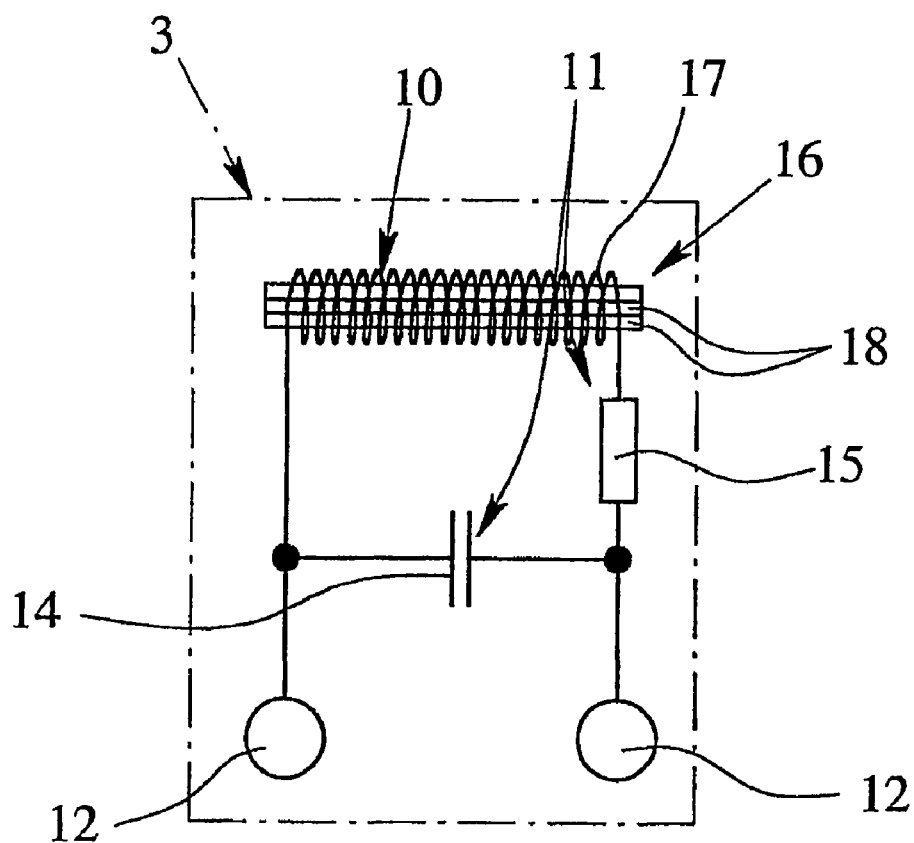
FIG. 4 is a block diagram of the electrode device according to this invention.

FIG. 4 shows a schematic block diagram of the electrode device 3 according to the described and preferred exemplary embodiment. In this case, the pulse forming device 11 preferably comprises a capacitance 14, in particular in the form of a capacitor, and a resistance 15. Additionally or alternatively, an inductance not shown, such as a coil can also be used for pulse forming.

The pulse forming device 11 is used for forming or reforming a pulse-like induction voltage which is generated or delivered under certain circumstances, as will be described in further detail hereinafter, by the induction or coil device 10. The reformed electrical impulse can then be output directly for stimulation via the connected electrodes 12.

Further structural elements are not required in principle but are possible. Furthermore, the electrode device 3 can also be implemented by other structural elements having a corresponding function.

The induction or coil device 10 is preferably configured such that a pulse-like induction voltage is generated when a minimum field strength of the, i.e., external magnetic field acting on the electrode device 3 or coil device 10 is exceeded. For this purpose, the coil device 10 particularly preferably has a coil core 16 which exhibits an abrupt change in the magnetization, i.e. bistable magnetic properties, when the minimum field strength is exceeded. This abrupt change in magnetization or magnetic polarization results in the desired pulse-like induction voltage in an allocated coil 17.

Figure 6:
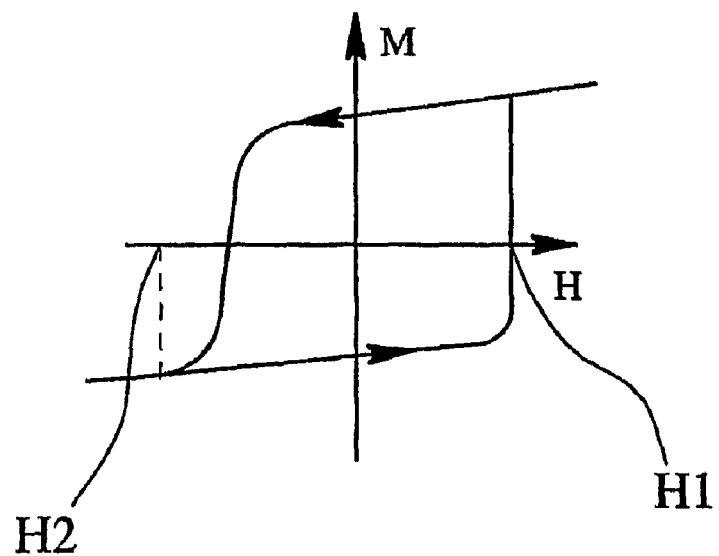
FIG. 6 is a schematic diagram of a magnetization curve of a coil device of the electrode device according to this invention.

In order to achieve the aforesaid bistable magnetic behavior of the coil core 16, as shown in the diagram according to FIG. 6 as an example, in the example shown the coil core 16 is preferably constructed of at least one core element 18, preferably of a plurality of core elements 18.

The core elements 18 preferably run parallel to one another so that the coil core 16 has a bundle-like structure of the core elements 18. If necessary, however, only a single core element 18 can be used to form the coil core 16, especially if the energy of the electrical impulse to be generated is relatively low or a different arrangement, for example, comprising a plurality of coil devices 10 is used.

Figure 5:
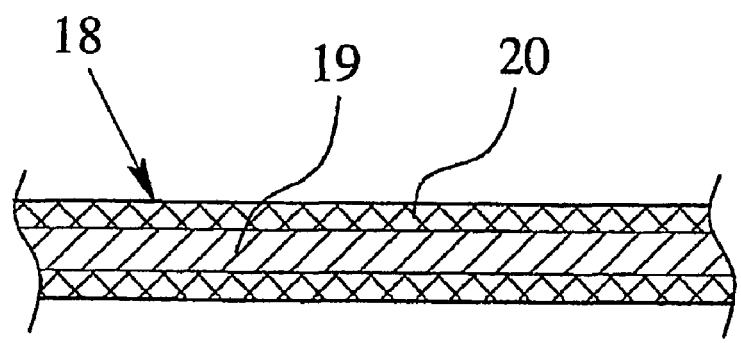
FIG. 5 is a schematic section view of a core element of the electrode device according to this invention.

FIG. 5 shows a preferred exemplary embodiment of the core element 18 in a sectional schematic view. The core element 18 is preferably configured as wire-like.

The coil core 16 and/or the core element 18 preferably have a layer arrangement of soft and hard magnetic material. In the example shown, an inner layer such as the core 19 and an outer layer such as the cladding 20 comprise of at least magnetically different materials, namely soft magnetic material on the one hand and hard magnetic material on the other hand. The differences therefore lie in the coactive field or in different hysteresis curves of the (magnetically) different materials. The coupling as a result of the layer structure then results in the desired magnetically bistable behavior or the desired abrupt change in the magnetization of the core element 18 or all the core elements 18 and therefore the coil core 16.

The individual core elements 18 preferably have a diameter of about 50 to 500 µm, in particular substantially 100 µm and/or a length of 5 to 20 mm, in particular substantially 15 mm.

The core elements 18 are particularly preferably so-called Wiegand wires as described in U.S. Pat. No. 3,820,090 and/or supplied by HID Corp., 333 St. Street, North, Heaven, Conn. 06473, USA under the trade name "Wiegand Effect Sensors" or so-called impulse wires as supplied by Tyco Electronics AMP GmbH, Siemensstrasse 13, 67336 Speyer, Germany. In the Wiegand wires the soft and hard magnetic layers are formed of the same material, the different magnetic properties being achieved in particular by mechanical reforming.

With regard to the possible structure and/or the materials used, reference is made supplementarily, additionally or alternatively to the article "Power Generating Device Using Compound Magnetic Wire" by A. Matsushita et al. published in the journal "Journal of Applied Physics", Vol 87, No. 9, 1 May 2000, page 6307 to 6309 and to the article "A Soft Magnetic Wire for Sensor Applications" by M. Vàzquez et al. published in the journal "J. Phys. D: Appl. Phys.", Vol. 29, 1996, pages 939 and 949, which are introduced as additional disclosure.

Various properties, features and operating modes of the proposed method, the proposed electrode device 3 and the proposed stimulation system 1 are explained in detail hereinafter.

The electrode device 3 for generating electrical impulses is preferably supplied with energy and/or controlled by means of a magnetic field H which can be generated in particular by the control device 2 in an exclusively wireless manner. In particular, the electrode device 3 requires no energy storage device such as a battery which restricts the lifetime of usability of the electrode device 3.

The electrode device 3 is configured such that an electrical impulse is only generated and delivered when a (first) minimum field strength of the magnetic field is exceeded. Furthermore, this or another pulse generation or triggering is preferably only made possible after respective previous activation.

The impulse generation and triggering preferably takes place as a result of the external magnetic field H acting on the coil device being varied in time so that when the first minimum magnetic field strength H1 is exceeded, an abrupt change in the magnetization of the core elements 18 or the coil 16 takes as shown in the schematic magnetization curve according to FIG. 6. As a result of the inverse Wiedemann effect, this abrupt change in the magnetization results in a pulse-shaped induction voltage (pulse P in FIG. 7) in the allocated coil 11. This first minimum field strength H1 is therefore a switching threshold.

The induced voltage pulses P can have an amplitude of up to about 5 V and are about 5 to 100 µs long. In order to achieve a preferably longer pulse duration, as is usual for cardiac stimulation, the optional pulse forming device 11 is preferably used. The induced voltage pulse P can thus in particular be stretched in time. Alternatively or additionally, a longer pulse duration can also be achieved by bundling a plurality of core elements 18 in the coil 17, in particular so that the pulse forming device 11 can be completely omitted.

Additional core elements 18 can be provided in the coil core 16 to increase the pulse power. Alternatively or additionally, a plurality of coil devices 10 can be connected in parallel or in series to increase the pulse power.

Alternatively or additionally, other magnetic, in particular permanent-magnetic elements can be used in the coil core 16 to achieve the respectively desired magnetic properties of the coil core 16.

The magnitude of the minimum field strength H1 depends on various factors, in particular the manufacturing conditions of the core elements 18. The minimum field strength H1 is preferably between 0.5 and 20 mT, in particular between 1 to 10 mT and is quite particularly preferably about 2 mT. These values are already substantially above the values for magnetic fields usually permissible in public so that any triggering of an electrical impulse by interference fields usually expected is eliminated.

The individual core elements 18 or the coil core 16 having the bistable magnetic properties, in particular in the preferred but not absolutely essential structure of layers having alternately soft and hard magnetic properties, can be used in various ways. In the example shown, preferably asymmetrical behavior is achieved on running through the magnetization curve or hysteresis. For resetting or attaining the starting point, that is activation for the triggering of the next impulse, the polarity of the coil core 16 is (completely) reversed by the external magnetic field H having the opposite direction when the second minimum field strength H2 is exceeded, as can be deduced from the magnetization curve in FIG. 6. It should be noted that in said processes in each case only the polarity of the soft magnetic material layers is reversed whilst the magnetization of the hard magnetic material layers is thus retained. In principle, however higher magnetic fields H can also be used to reverse the polarity of the hard magnetic layers if required.

In the example shown, the external magnetic field H, in particular generated by the control device 2, is used both for controlling (triggering) the generation and delivery of an electrical impulse by the electrode device 3 and also for supplying the electrode device 3 with the energy necessary for generating the electrical impulse. In addition, the magnetic field H is preferably also used for said activation of the electrode device 3 for the possible generation of the next electrical impulse. However, this can be also be effected in another manner or by another signal.

The external magnetic field H preferably runs at least substantially parallel to the longitudinal direction of the coil core 16 or the core elements 18.

Figure 7:
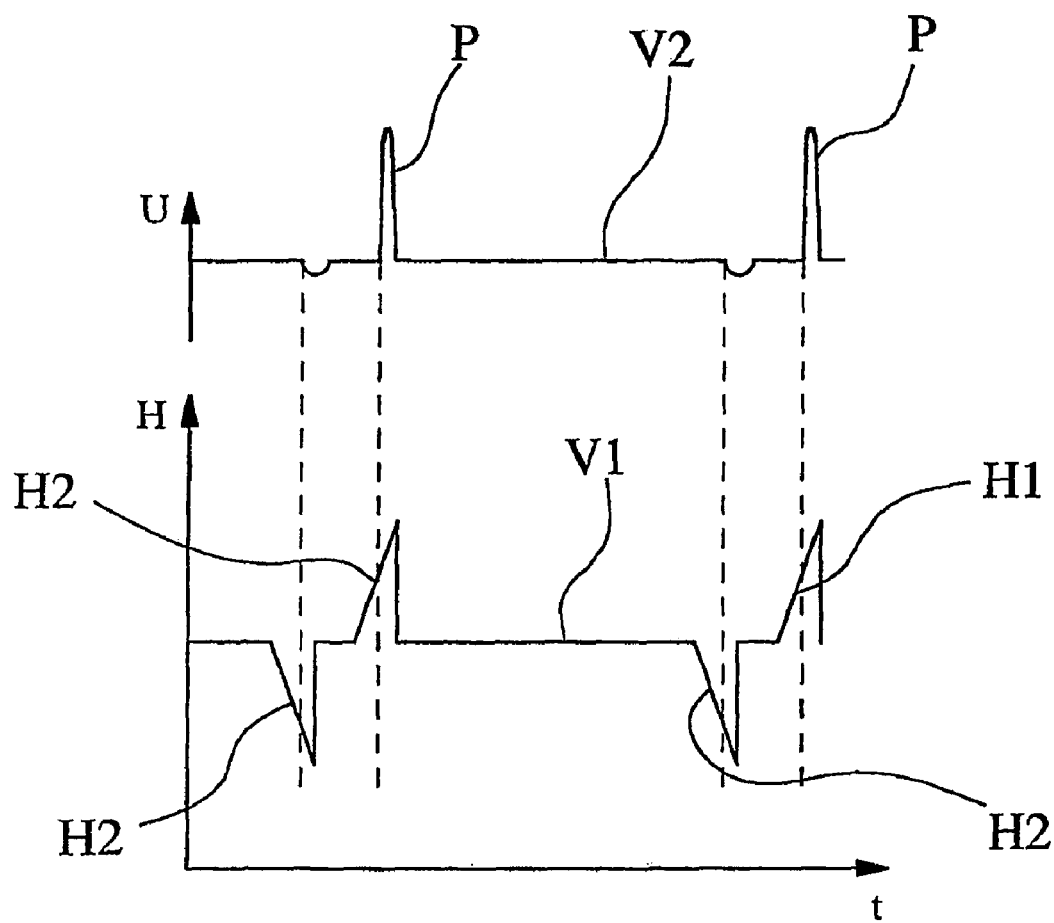
FIG. 7 is a schematic diagram of the time profile of a magnetic field and an induced voltage according to this invention.

FIG. 7 shows schematically a preferred time profile V1 of the external magnetic field H acting on the electrode device 3 and the corresponding time profile V2 of the voltage U induced in the electrode device 3 or its coil 17.

The magnetic field H is preferably generated intermittently and/or as an alternating field. The magnetic field H preferably has a switch-on ratio of less than 0.5, in particular less than 0.25, particularly preferably substantially 0.1 or less.

The field strength of the magnetic field H has a substantially ramp-shaped or sawtooth-shaped time profile, at least during the switch-on times as indicated in FIG. 7.

The magnetic field H is alternately generated with an opposite field direction for alternate generation of an electrical impulse and activation of the electrode device 3 before generation of the next electrical impulse. The activation preferably takes place only shortly before generating the next electrical impulse, as indicated in FIG. 7.

The frequency of the magnetic field H is preferably only a few Hz, in particular less than 3 Hz and corresponds in particular to the desired frequency of the electrical impulses to be generated.

The ramp-shaped increase in the field strength of the magnetic field H is preferably relatively steep in order to achieve only short switch-on times and only a low switch-on ratio. This is advantageous in regard to minimizing the required energy and a defined triggering with few interfering influences.

According to the minimum field strength to be achieved, the maximum field strength of the magnetic field H in the region of the electrode device 3 preferably reaches substantially 1 to 20 mT, in particular 2 to 10 mT.

It can be seen from FIG. 7 that the negative magnetic field ramps on reaching the second minimum field strength H2 in each case only induce a very small electrical impulse which is negligible compared to the pulses P at the abrupt change in magnetization. The magnitude of these small pulses depends substantially on the rate of change in the magnetization during resetting, that is during the activation of the electrode device 3 for generation of the next electrical impulse.

According to a further development not shown, a plurality of electrode devices 3 can be used which in particular can be controlled and supplied with energy by a common control device 2. The electrode devices 3 can then be implanted at different locations, for example. As a result of different first minimum field strengths H1, different coil devices 10 and/or pulse forming devices 11 or the like, desired phase shifts, energy differences or the like can then be achieved in the electrical impulses or signals delivered by the individual electrode devices 3.

It should be noted that the preferred synchronization of the stimulation of the heart 6 with the heat beat can be achieved, for example, by evaluating the electric voltage induced in the coil 7 of the control device 2 by the movement of the electrode device 3, optionally in conjunction with the ECG voltage which can be detected galvanically via the housing of the control device 2 or a relevant electrode.

Particular advantages of the invention reside in the possibility that the wireless electrode device 3 can be implanted in more suitable regions for stimulation, in particular, of the heart muscle, than is possible with wire-bound electrodes. Moreover, a plurality of electrode devices 3 can be implanted at different locations whereby improved stimulation and in particular better cardiac dynamics can be achieved.

Figure 8:
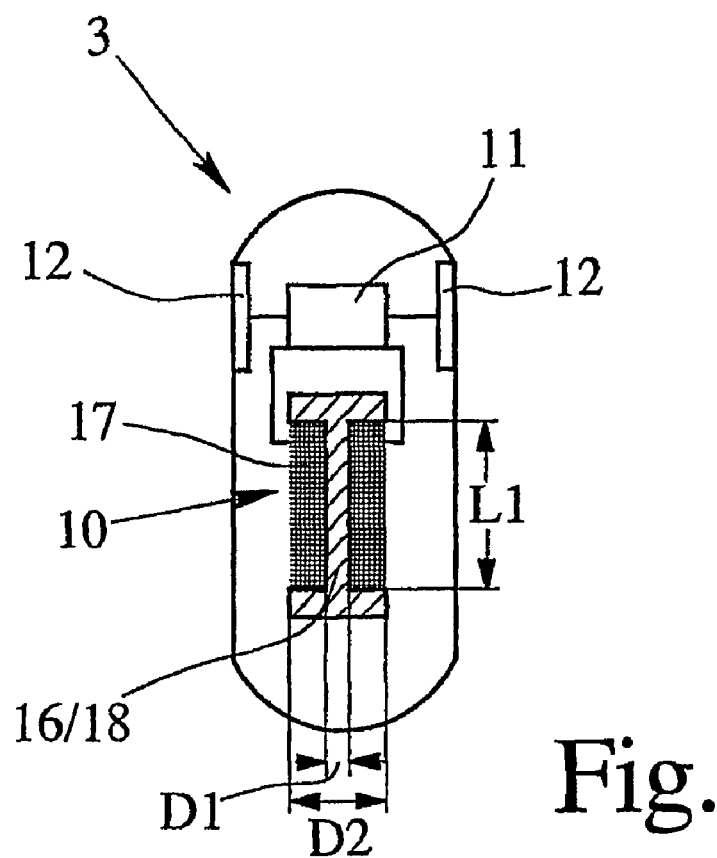
FIG. 8 is a schematic section of another electrode device according to this invention.

FIG. 8 is a schematic section of a further embodiment of the proposed electrode device 3. In this case, the coil device 10 can comprise a coil core 16 or core elements 18 made of a soft magnetic material or ultrasoft magnetic material, for example in the form of wires or strips. Such a material has a very low coactive field strength which corresponds to the minimum field strength H1 and in particular is less than 0.1 mT. The saturation field strengths of the material are less than about 0.01 to 3 mT. The coil core 16 consists of non-magnetic or completely or partially of said soft magnetic or ultrasoft magnetic material or a combination of various such magnetic materials.

In this case, the electrode device 3 or coil device 10 comprises a coil 17 preferably having a high number of turns, in particular at least 1,000 turns, particularly preferably 2,000 turns or more. In the example shown, the coil 17 has substantially 3,000 turns or more.

In the example shown, the coil inside diameter D1 is preferably 1 to 3 mm, the coil outside diameter D2 is preferably 2 to 6 mm and the coil length L1 is preferably 10 to 30 mm.

In general, ferrites or ferromagnetic metal powder materials can be used as core materials or soft magnetic materials. An advantage is that as a result of the poor electrical conductivity, these materials only exhibit low eddy current losses.

In general, the bobbin-like coil shown in FIG. 8 or its core 16 or only the central rod or only a rod-shaped core 16 or a plurality of core elements 18 can be constructed of soft or ultrasoft materials in the form of a stack of films electrically insulated from one another to reduce the transverse conductivity, to minimize eddy current losses. The same applies to the use of ferrites or other materials having corresponding properties.

The proposed electrode device 3 or coil device 10 permits the generation of relatively strong electrical impulses, in particular an impulse having a voltage of at least 1 V and a time duration of substantially 0.1 ms or more. This can be achieved in particular by the bobbin-like coil configuration shown and/ or by the high number of turns. In particular, this relatively strong and relatively long-lived electrical impulse can also be achieved with the soft magnetic core material. A magnetic resetting pulse as with the Wiegand wires or the like is not absolutely necessary. However, a combination with the other magnetic materials or structures is possible.

As a result of the special RLC properties (impedance) of the primary coil 7, the exciting magnetic field H can only increase relatively slowly (typically from 0 to a maximum of, for example, 0.1 to 2 mT in 0.1 to 5 ms). In the proposed coil device 10 and under loading with a characteristic resistance for the heart muscle of, for example, about 1 kOhm, a relatively broad or long-lived impulse having a duration of at least 0.1 ms, in particular of substantially 0.25 to 2 ms, can be generated. This can possibly be attributed to the alternating current properties of the LRC arrangement (or the coil device 10, high inductance and high winding capacity of the coil) and/or to the retroactive effect of the coil current on the core 16.

The electrode device 3 described hereinbefore is preferably again combined with the control device 2 already described or another control device 2 and/or is controlled and/or supplied with energy preferably exclusively by means of an external or varying magnetic field H, as already described.

Figure 9:
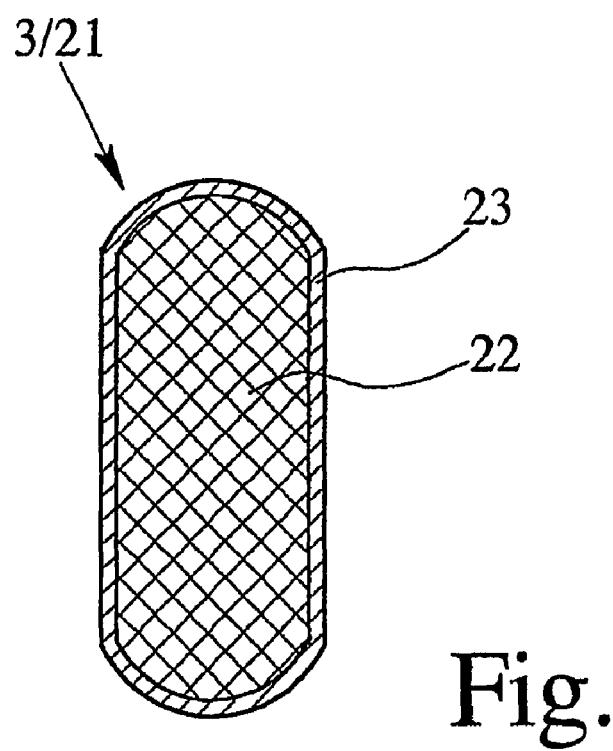
FIG. 9 is a schematic section of another stimulation or electrode device according to this invention.

FIG. 9 shows another embodiment of the proposed electrode device 3. More precisely, this is not an electrode device 3 but a stimulation device 21 since no electrodes 12 are required as in the preceding embodiments. However, the stimulation device 21 can be used instead of the electrode device 3 or for the stimulation system 1 described previously. The reasoning so far relating to the use and insertion of the electrode device 3 therefore fundamentally apply accordingly for the stimulation device 21.

The stimulation device 21 has a magnetisable element 22 which is preferably surrounded by an optional cladding 23. Electrodes 12 or the like as in the electrode device 3 are preferably not required.

The element 22 can be magnetized by an external or varying magnetic field H, in particular, the magnetic field H is generated by the control device 2 or in another suitable manner.

Variation of the magnetic field H causes a change in the magnetization of the element 22. Accordingly, the magnetic leakage flux of the element 22 in the tissue surrounding the stimulation device 21 in the implanted state, such as the heart 6, varies in time so that an electrical field strength or an electrical stimulation is generated. Consequently, an electrical stimulation or an electrical impulse is generated in the tissue, such as the heart 6, without electrodes 12.

The element 22 is preferably ferromagnetic, in particular at least substantially or exclusively made of ferromagnetic material. Alternatively or additionally, the element 22 can also be constructed as described with reference to FIG. 5 and/or it can be constructed as a Wiegand wire or the like and/or from a plurality or a bundle of core elements 18.

The stimulation device 21 in particular brings about an amplification of the external magnetic field H at the location of the stimulation device 21, that is at the implanted site. This makes it possible to achieve specific electrical stimulation in the desired area and/or depending on the magnetic field H.

Figure 10:
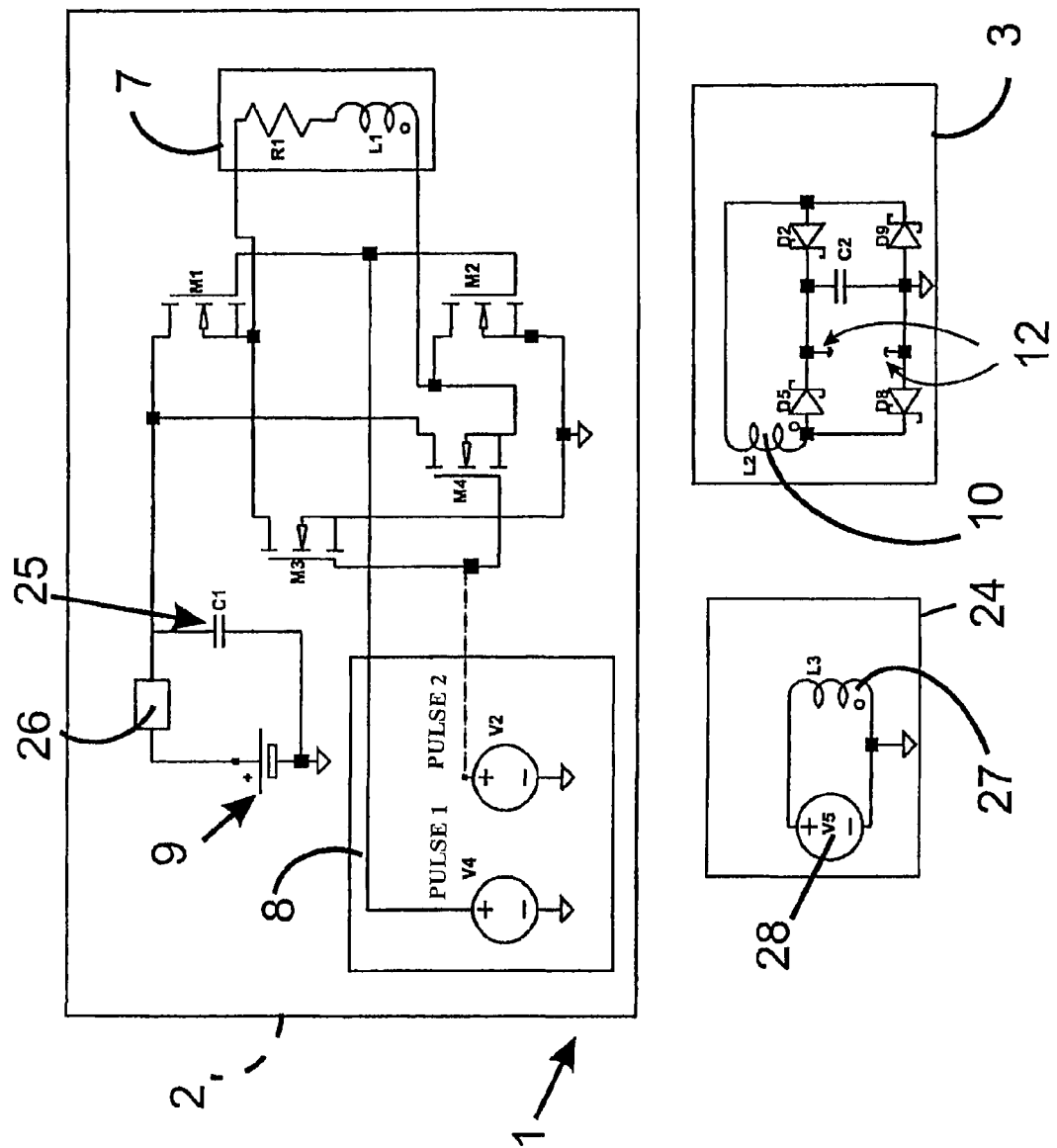
FIG. 10 is a schematic block diagram of a further proposed stimulation system comprising control device and electrode device as well as comprising a charging device according to this invention.

FIG. 10 shows another embodiment of the proposed stimulation system 1 comprising the control device 2, the electrode device 3 and an external charging device 24 in a schematic diagram similar to a block diagram. In this embodiment a plurality of short magnetic field pulses are generated as a sequence by the control device 2 during the switch-on time of the magnetic field H, i.e. during the switch-on phases. In particular, it is thus achieved that the coil arrangement 10 or its coil core 16 always changes its magnetization far below the saturation state. Thus, a minimum energy consumption can be achieved since the largest possible flux variation in the core of the coil arrangement 10 of the electrode device 3 is present or produced during the entire switch-on time of the magnetic field H and therefore substantially during the generation of the electrical impulse.

The magnetic field pulses can be unipolar or bipolar when using soft magnetic core materials. Bipolar magnetic field pulses are used when using bistable materials.

In the example shown according to FIG. 10, bipolar magnetic field pulses are preferably generated by means of a bridge of switching transistors M1 to M4 (e.g. MOSFETS, also in complementary design) or other switching semiconductor components. Also indicated in FIG. 10 are the coil 7, the control 8 and the energy storage device 9 of the control device 2. The control 8 can, for example, comprise one or two signal generators V2 and V4. Preferably connected in parallel to the energy storage device 9 is a smoothing capacitor 25. In addition, separating electronics 26 such as a switch or the like can be provided.

The control device 2 or its coil 7 is preferably configured such that the control device 2 or its energy storage device 9 can be inductively charged in the implanted state, in particular via the coil 7. For generating the required electromagnetic field during charging the charging device 24 is equipped with a suitable coil 27 and a corresponding power supply, in particular an alternating current supply 28.

In one exemplary embodiment, multiple magnetic field pulses are used to control the electrode device 3 and to generate the respectively desired electrical impulses, i.e. multiple magnetic field pulses form one single electric pulse for one stimulation.

The exemplary electrode device 3 can comprise a rectifier (in FIG. 10 formed by the shown diodes or any other components diodes, in particular with a means for smoothing the resulting electrical voltage, here in the form of a capacitance). Thus, a single electrical impulse can be generated as desired, in particular as discussed in the following with regard to FIG. 11.

FIG. 11a) is a schematic diagram showing a possible pulse sequence (voltage over time t) generated by the control 8 and allowing optimum triggering of the bridge. The trigger pulses, in this case for the bridge of switching transistors, are preferably only generated during the switch-on time $t_{on}$ to $t_{off}$, i.e. when the magnetic field H is switched on. For example, the trigger pulses each last less than 50 μs. After a first pulse 1 (shown by the continuous line) and a certain delay time of, for example, $\Delta t_1$ of about 1 to 10 μs, an opposite pulse 2 then follows for the duration $t_2$ which in particular corresponds to the first duration $t_1$, and which reverse the primary coil voltage (voltage of the coil 7) via the bridge. This alternating generation of trigger pulses is repeated n times until a sufficient number of pulses consisting of positive and negative paired single pulses has been delivered.

Figure 11:
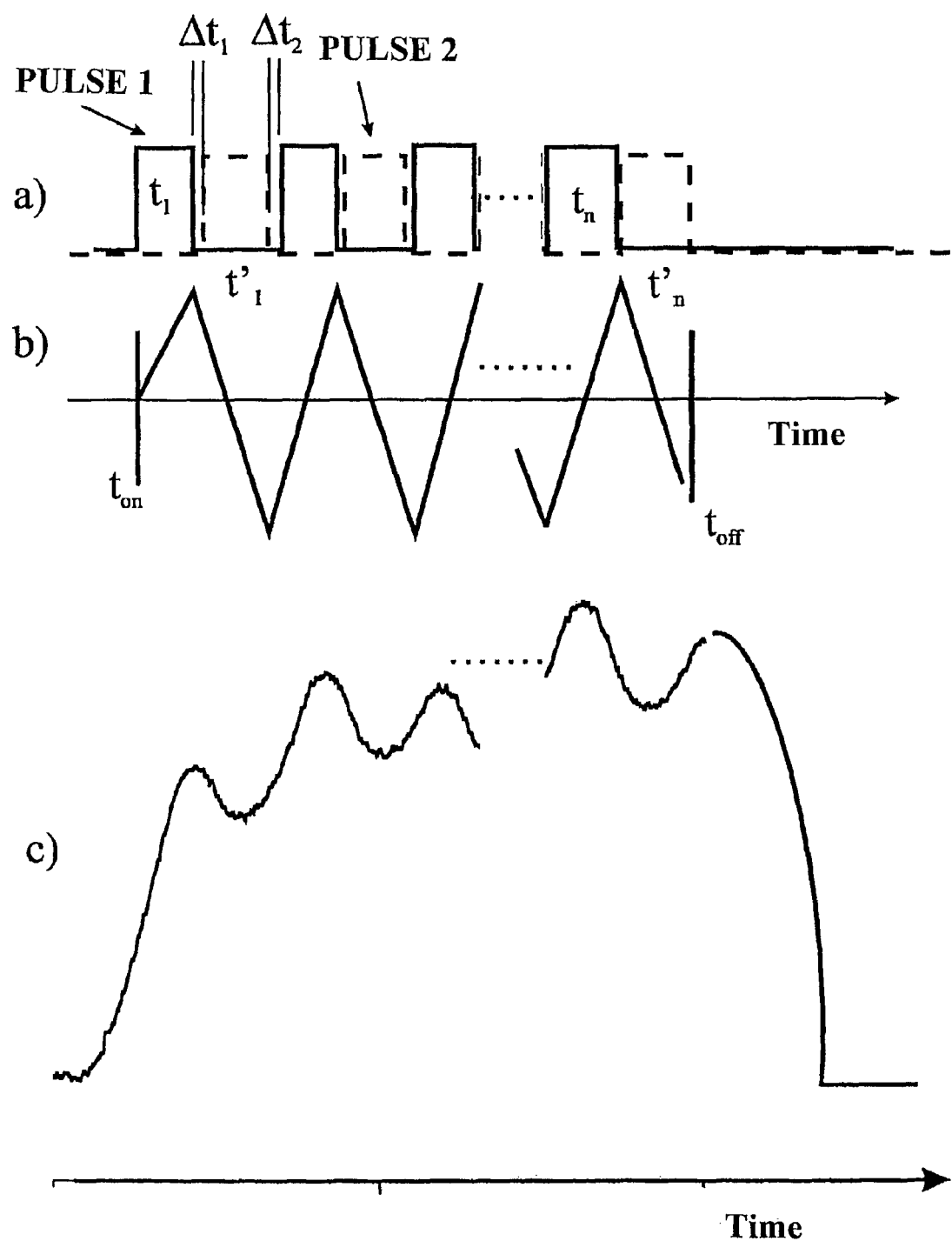
FIG. 11a-c is a schematic diagram of the time profile of trigger pulses, a generated magnetic field and a generated electrical impulse according to this invention.

As a result of the inductance of the coil 7, the trigger pulses or pulse sequences shown results in a sequence of in particular at least substantially sawtooth-shaped, preferably bipolar magnetic field pulses (shown as current through the coil 7 over time t in FIG. 11 b) which act on the electrode device 3 or its coil device 10 (secondary coil) as the magnetic field H in the sense of the present invention and there bring about the generation of an electrical impulse (or a sequence of electrical impulses for each single stimulation) for stimulation. FIG. 11c) shows an electrical impulse (in particular a superposition of partially smoothed individual impulses) generated by the magnetic field pulses or the pulse-like varying magnetic field H as a schematic diagram of voltage over time t. In particular, the length of the electrical impulse depends on the length of the switch-on time of the trigger pulses or the magnetic field pulse and substantially corresponds particularly preferably to the switch-on time.

Similar behavior can be achieved with a unipolar sequence of magnetic field pulses. In this case, for example, the left part of the bridge and the generator V2 in FIG. 10 as well as the dashed pulse sequence 2 in FIG. 11 c) can be omitted.

The duration between two trigger pulses Δt should be selected so that the second pulse is triggered when the primary coil current which initially decreases quasi-linearly towards zero, reaches the zero level. This time interval depends both on the R/L value of the coil 7 and on the R/L value of the secondary circuit, in particular the coil arrangement 10. For the primary circuit (control device 2) substantially the winding resistance and the inductance of the coil device 10 determine the R/L ratio whilst the resistance of the coil device 10 is determined by the winding resistance and the loading resistance (tissue resistance of the stimulated part of the heart muscle or the like which is present at the electrodes 12) and the inductance is determined by the winding inductance taking into account the preferably ferromagnetic core 16. Here R designates the electrical resistance in general and L designates the inductance.

As has been explained, the impulses induced in the coil device 10 at times t or t' have different signs, i.e. a pulse sequence of bipolar pulses is obtained (both in the case of unipolar and bipolar excitation by magnetic field pulses). Unipolar electrical impulses are preferably required and generated for stimulation. These are rectified by a rectifier, in particular a bridge or diode rectifier, in the electrode device 3. The rectifier is preferably connected between the connections of the oil device 10 and the electrodes 12, as indicated in FIG. 10. This results in unipolar sequences of electrical impulses with peak values. Between the peak values the voltages can be close to zero. A small smoothing capacitor C2 (of, for example, 1 to 100 nF) connected in parallel to the stimulation electrodes can smooth this pulsating voltage sequence if necessary. The capacitance can be optimally matched to the properties of the entire system.

With regard to FIG. 10, it should be noted that the electrode device 3 is preferably only constructed of passive, in particular, few components such as one or a plurality of diodes, in particular Schottky diodes D2, D5, D8, D9 to form the rectifier and/or the capacitor C2.

The duration of the respective electrical impulse (a single stimulation) generated by the electrode device depends on the respective switch-on time of the magnetic field H, in particular on the number of trigger pulses generated in a sequence and thus on the number of magnetic field pulses generated by the control device 2. Consequently, the control device 2 controls the generation of the electrical impulse or the electrode device 3 by the magnetic field H directly in the initially specified sense of the present invention.

The schematic diagram according to FIG. 11 c) shows the influence of the rectifier and the R/L ratio of the coil device 10 of the electrode device 3. When the R/L ratio is large (e.g. very small L), the coil voltage follows the derivative of the primary coil current dI/dt, which preferably increases or decreases quasi-linearly here as a consequence of the smaller R/L ratio of the primary coil (coil 7) when the polarity of the primary coil voltage is reversed. When the R/L ratio of the coil device 10 is small (including the tissue resistance present at the electrodes 12), as is realistic on account of the preferred high number of turns (in particular about 1,000 turns or more) and the preferred presence of the ferromagnetic core 16, the induced coil voltage (measured as the voltage at the load resistance of the coil 17—in particular therefore at the tissue resistance present at the electrodes 12) only increases relatively slowly.

The proposed method of using relatively short, closely following, rectified electrical impulses as a result of a sequence of short magnetic field pulses or trigger pulses according to FIG. 11 to stimulate a single heart beat or the like offers the possibility of adapting the stimulation pulse duration (the total length of the electrical impulse during a switch-on time of the magnetic field H, substantially the switch-on time $t_{on}$ to $t_{off}$) to the needs of a particular patient by suitably adjusting the number n of pulse pairs of the trigger pulses by acting externally on the control 8 equipped with at least one suitable sensor. However, other electrical or electrotechnical design solutions are also possible.

Figure 12:
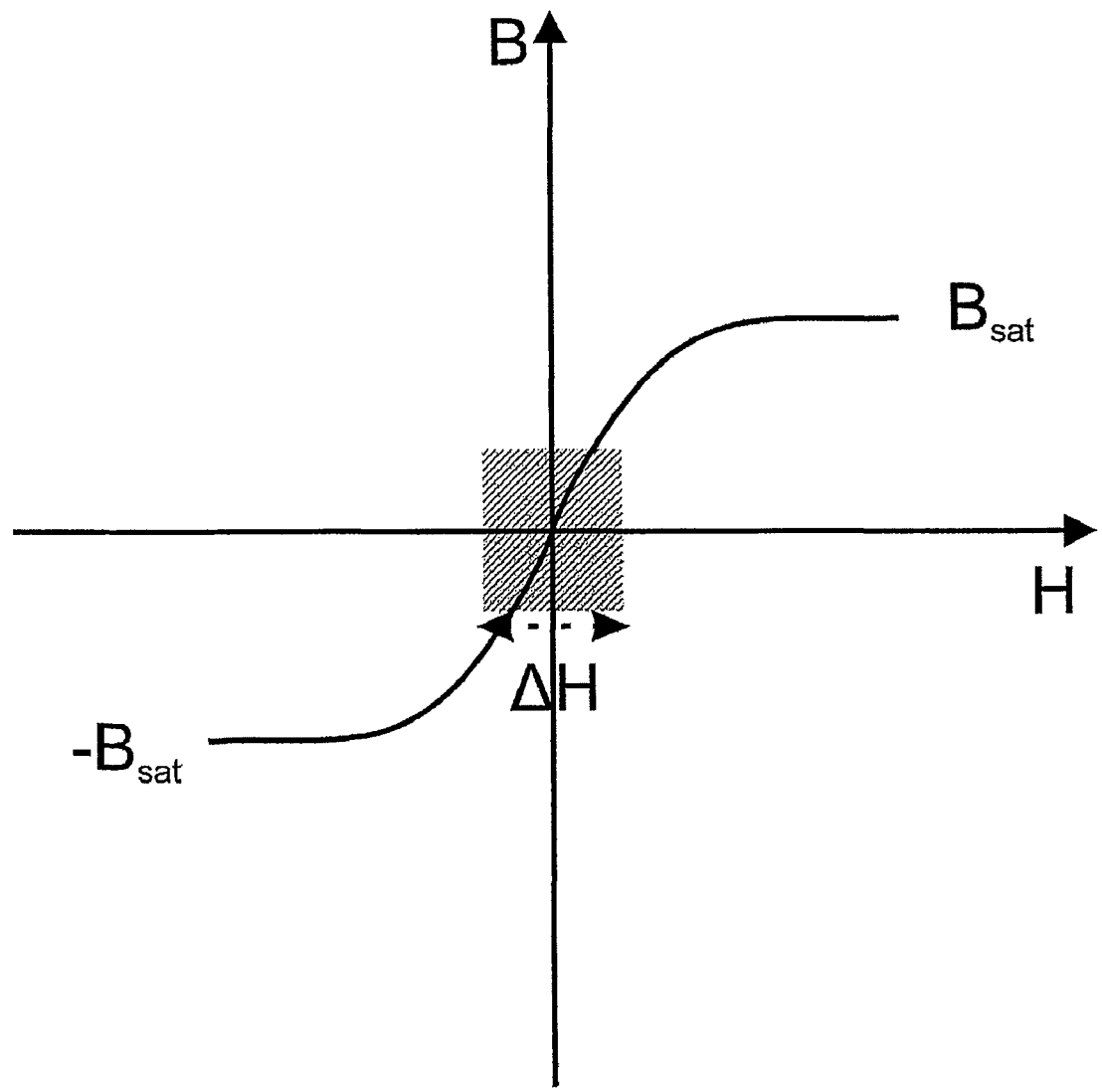
FIG. 12 illustrates an example of an exemplary magnetization according to this invention.

FIG. 12 shows a B(H) curve (schematic). ΔH corresponds to the current variation through the primary coil produced by applying a voltage pulse to its leads. Symmetry to H=0 is achieved by using a sequence of a positive and a negative voltage pulse of equal amplitudes (cf. FIG. 11). This is advantageous to the case of using a unipolar voltage pulse producing the same ΔH since dB/dH is monotonically decreasing along the hysteresis curve. Hysteresis effects have been omitted in the drawing since core materials with very small hysteresis are to be preferred to avoid BH-losses.

A constant voltage suddenly applied to the primary coil results in a monotonically increasing current through the coil (Eq. 1) and hence a proportionally increasing magnetic field at the site of the electrode device 3 the rate governed by the time constant L/R of the coil circuit.

$$i = U/R \cdot \left(1 - e^{\frac{-t}{L/R}}\right) \qquad \text{(Eq. 1)}$$

Since the induced voltage in the coil device 10 of the electrode device 3 is proportional to the change of the induction dB/dt in the core element 18 which is a function of H, the induced voltage decreases with time during the time the voltage pulse at coil 7 is on. This means a reduction of the efficiency of conversion of the electric power consumed by coil 7 into a voltage occurring at the posts 12 the longer the voltage is applied to coil 7. Therefore, for optimal efficiency, H should be kept small which is reached by switching off or reversing the voltage applied to coil 7 by using short pulse duration times.

The amplitude and duration of the induced voltage pulse in the coil device 10 is adjusted by choosing a proper pulse voltage applied to coil 7, a suitable pulse duration and frequency. A very high frequency becomes undesirable to one part because of an increased impedance of the stimulator coil ($Z = \omega \times L$), resulting in reduced pacing pulse amplitudes. For a given design of the coil 7 and the electrode device 3 at a given mutual geometric arrangement (including the distance of the electrode device 3 from the plane of the coil 7, the angle between the coil axis and the distance of the electrode device 3 from the axis of the coil 7) details of the burst pulse sequence are optimized for minimal energy consumption at a desired pacing pulse shape. The energy consumption is given by $$E = \tfrac{1}{2} C (U_1^2 - U_2^2)$$

where $U_1$ is the voltage at the charging capacitor C before firing a pulse burst and $U_2$ the voltage after firing a pulse burst after the power supply has been disconnected from C.

Figure 13:
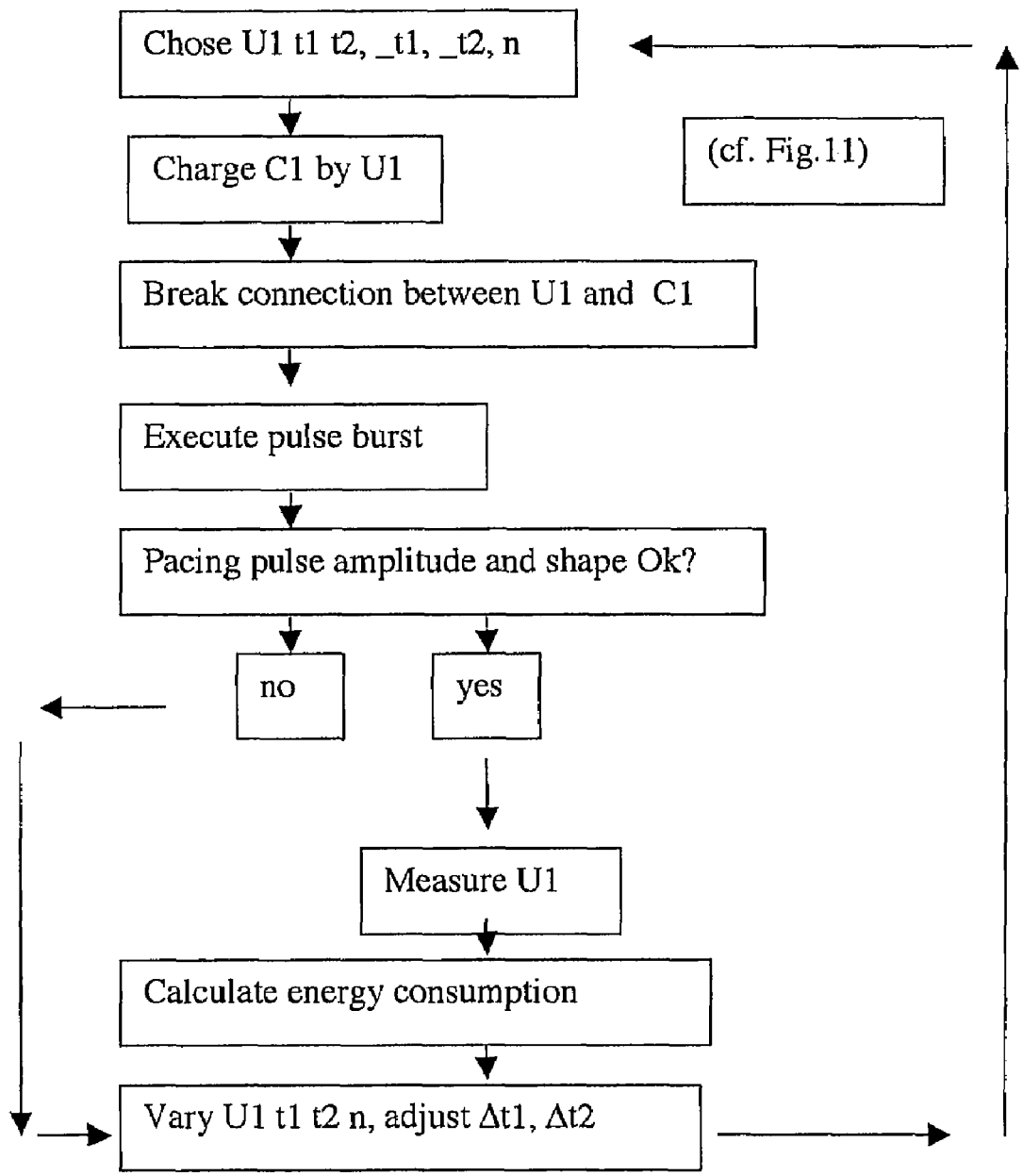
FIG. 13 is a diagram for choosing optimized operation parameters according to this invention.

Since the electronic properties of the electrode device are strongly non-linear and only approximately known a priori, the optimal operational parameters of the pacing system have to be determined experimentally. This is performed for a single pacing pulse preferably according to the diagram shown in FIG. 13.

The timing sequence of the voltage pulses comprising a burst applied to the coil 7 can be chosen to produce almost arbitrary pacing pulse shapes. For instance, a ramp-like increase of the pacing pulse is obtained with sequentially increased voltage pulse amplitudes.

Figure 14:
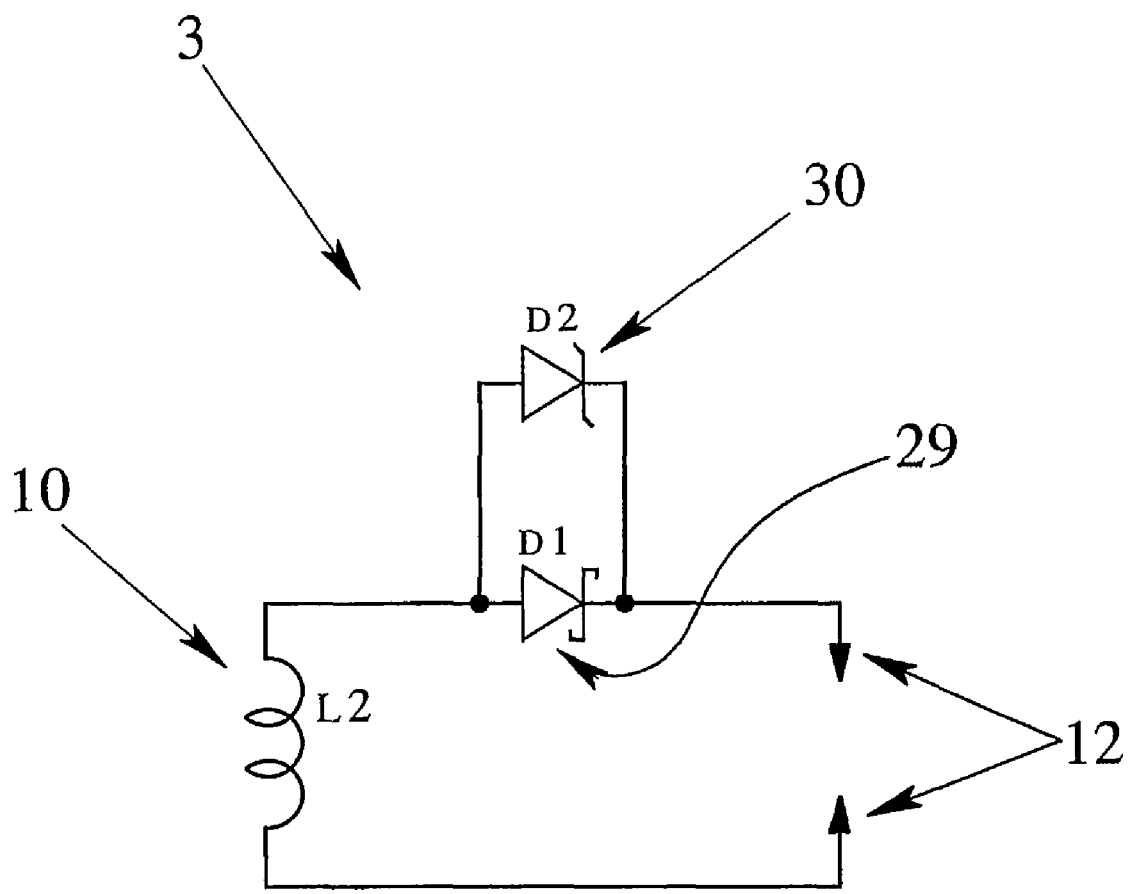
FIG. 14 is a schematic diagram of an exemplary circuit of the electrode device according to the present invention.

Especially, the pacing pulse can be made to change sign for some arbitrary fraction of time. This may be achieved by using a one-way rectifier 29 or diode D1 instead of the bridge rectifier depicted in FIG. 11 and attaching or connecting a Zener diode 30 (or other devices exhibiting a breakdown characteristic like four-layer-diodes, thyristors, etc.) parallel to the rectifying diode D1 with an adequate Zener voltage larger than that of the normal rectifying diode, as shown in the exemplary embodiment in FIG. 14.

Whenever the induced voltage, now with an opposite sign as compared the normal pulse, is increased beyond the Zener breakdown voltage (or the Off-State Voltage of the mentioned other types of semiconductors) a reversed pulse polarity is obtained. This requires producing an asymmetrical rate of current increase or decrease through the coil 7, i.e., producing di/dt values differing in sign and amplitude. Hence the amplitudes of positive and negative induction voltages in the electrode 3 will be different, enabling the selective application of positive or negative pacing pulses. The differing di/dt values are obtained by applying voltage pulses U (cf. Eq. 1) of different amplitudes and polarities to the coil 7. The described possibility is advantageous since the pacing voltage is reported to increase with time when pacing with unipolar pulses. This potentially undesirable effect is largely reduced by employing a bipolar pacing pulse. The possibility to produce arbitrary bipolar pacing pulses persists when the normal diode D1 is omitted, using the forward and breakdown characteristics of the Zener diode.

In particular, the following aspects of the present invention can be realized independently or in any combination:

An exemplary embodiment of the present invention makes use of energy recovery by the magnetic field.

An exemplary embodiment of the present invention uses parameters and operations such that core magnetic saturation in the electrode 3 is avoided. This reduces energy consumption significantly.

The pulse shape can be adjusted arbitrary for the most effective stimulation with respect to the pacing pulse height and width by using a programmable sequence of amplitudes, durations and delay times of the individual burst pulse voltages (voltage source 9, our FIG. 10) applied to the primary coil. The importance of choosing an optimal pulse shape has been described in U.S. Pat. No. 5,782,880 A.

This very flexible design also provides the possibility to generate bipolar pacing pulses by controlling the di/dt rate and sign of the current sent through the primary coil 7 and making use of Zener diodes or other rectifiers with selectable breakthrough voltages.

The burst-pulse sequence is optimized with respect to duration, repetition rate and time delay to achieve minimal energy consumption for a given pacing pulse amplitude an duration. If, e.g., the delay times $\Delta t_1$ or $\Delta t_2$ are too small, the energy consumption can increase dramatically.

Use of Cu cladded Al strand (Litz) wire in the primary coil is preferred and of advantage for significantly reducing the weight of the coil of the electrode device. It also provides—as also does Cu strand wire—a large degree of mechanical flexibility. Due to the skin effect present because of the alternating current sent through coil 7 the effect of the smaller conductivity of the Al as compared that of Cu is reduced but the weight is determined largely by the aluminum. In an experiment, the energy consumption using the Co cladded Al Litz wire was close to that of using pure Cu Litz wire with similar dimensions.

Metallic soft or ultrasoft magnetic cores might preferably be used for the electrode device and provide a larger saturation magnetization as compared to ferrite. Accordingly, a lower exciting magnetic field will be needed. Due to the transients of the magnetic field pulses eddy current losses occur in the core material. They are essentially reduced by lamination of metallic cores which is preferred.

Magnetically soft cores can be achieved in particular by lamination of multiple isolated layers. Magnetically ultrasoft cores can be achieved in particular by using amorphous or nanocrystalline magnetic materials.

Only one cap at the side of the stimulator that points toward the primary coil on the core instead of two, making it smaller and only slightly less efficient.

It is preferred to use energy recovery of the magnetic field by using high capacity buffering (supercaps) of the power supply together with fast switching diodes parallel to the MOSFETs comprising the H-bridge (FIG. 11) in case these are not already implemented in the MOSFETs. This also extends the lifetime of the batteries since the large peak currents are delivered by the supercaps instead of the battery.

The control device is preferably in a flexible housing as it should be implanted directly above the heart near the thoracic wall. To achieve this flexibility the control device can be embedded in a silicon cushion, however other soft materials can also be used.

For magnetic field concentration towards the electrode 3 a flux concentrator might be used contained within the interior of the inner surface of the preferably soft housing, preferably silicon cushion. Experiments had shown an increase in magnetic field strength at the pacing site when the coil 7 was halfway surrounded by a thin Mumetal cover the collar of which pointing to the pacing site. Other shapes might be used.

To guarantee flexibility the power supply should be preferably provided by tailor made, flexible, lithium polymer batteries. However also other types of power supplies might be used (thermoelectric using body heat, fuel cells, cells using body fluids, or the like).

An exemplary embodiment, the electrode devices comprises a flexible housing and/or means for magnetic field concentration at the inner surface of the housing as described above.

The induction pacemaker technology described can also be used in combination with conventional cardiac pacemaker technology. In this connection, the use for left-ventricular stimulation within the framework of resynchronization therapy is particularly appropriate.

Individual features, aspects and elements of the individual embodiments and variants can be arbitrarily combined with one another or used in other stimulation systems or electrode devices.

What is claimed is:

1. A stimulation system comprising an implantable control device and an implantable electrode device for generating electrical impulses, which can be supplied with energy and controlled by the control device in an exclusively wireless manner by means of a time-varying magnetic field, the control device being configured such that the field strength of the magnetic field, at least during switch-on times, has a substantially ramp- or sawtooth-shaped time profile or is bipolar or pulsed; and wherein the stimulation system is configured in such a manner that in the switched-on state the magnetic field is formed by a plurality of unipolar or bipolar magnetic field pulses and/or that the respective switch-on duration of the magnetic field controls or determines the length of each electrical impulse of a stimulation generated by the electrode device and/or the magnetic field is utilized for energy recovery.

2. The stimulation system according to claim 1, wherein the control device is configured such that the magnetic field is at least of generated intermittently and comprises a switch-on ratio of:

less than 0.5;
less than 0.25; or
less than approximately 0.1.

3. The stimulation system according to claim 1, wherein the control device is configured in such a manner that the magnetic field is alternately generated with an opposite field direction for the alternate generation of an electrical impulse and activating the electrode device before generating the next electrical impulse, in particular wherein the activation takes place shortly before generation of the next electrical impulse.

4. The stimulation system according to claim 1, wherein the frequency of the magnetic field is less than 3 Hz or corresponds to the desired frequency of the electrical impulses to be generated.

5. The stimulation system according to claim 1, wherein the control device is configured in such a manner that the field strength of the magnetic field in the region of the electrode device is substantially 1 to 20 mT.

6. The stimulation system according to claim 1, wherein the control device in the implanted state can be charged inductively from outside.

7. The stimulation system according to claim 1, wherein the stimulation system is a cardiac pacemaker.

8. The stimulation system according to claim 1, wherein the electrode device is configured in such a manner that an electrical impulse can be generated in each case only following previous activation, in particular by exceeding a second minimum field strength of the magnetic field having the opposite field direction to the field direction for the generation of an electrical impulse, in particular wherein the second minimum field strength is greater than the first minimum field strength.

9. The stimulation system according to claim 1, wherein the electrode device comprises a coil device which generates a pulse-like induction voltage when a first minimum field strength of the magnetic field is exceeded, in particular wherein the coil device comprises at least one of a coil core or a core element having a magnetization which varies abruptly depending on the acting magnetic field strength and a wire-like layer arrangement of soft and hard magnetic material.

10. The stimulation system according to claim 1, wherein the electrode device comprises a coil device, wherein an electrical impulse having a voltage of at least 0.5 V and a time duration of at least 0.05 ms can be generated by the coil device by at least one of an external and a varying magnetic field having a field strength in the region of the electrode device of at most 10 mT.

11. The stimulation system according to claim 1, wherein the electrode device preferably comprises only a passively operating pulse forming device, in particular having at least one of an inductance, a capacitance and a resistance, wherein the electrode device is configured as at least one of a battery-less and amplifier-less device, wherein the electrode device comprises a coil device with a magnetic core, the core being magnetically soft or ultra-soft.

12. The stimulation system according to claim 1, wherein the electrode device is configured such that each pulse-like induction voltage is output as an electrical impulse via integrated electrodes.

13. The stimulation system according to claim 1, wherein the electrode device comprises a coil device with a magnetic core, the core being at least one of magnetically soft and ultra-soft.

14. An implantable electrode device for a stimulation system for generating electrical impulses, wherein the electrode device is configured as at least one of a wireless and a compact structural unit, and can be supplied with energy and directly controlled exclusively by means of a varying magnetic field, wherein the electrode device is configured in such a manner that an electrical impulse is only generated when a first minimum field strength of the magnetic field is exceeded.

15. The electrode device according to claim 14, wherein the electrode device is configured in such a manner that an electrical impulse can be generated in each case only following previous activation.

16. The electrode device according to claim 15, wherein an electrical impulse can be generated in each case only following previous activation, by exceeding a second minimum field strength of the magnetic field having the opposite field direction to the field direction for the generation of an electrical impulse.

17. The electrode device according to claim 14, wherein the minimum field strength is substantially 0.5 to 20 mT.

18. The electrode device according to claim 14, wherein the electrode device comprises a coil device which generates a pulse-like induction voltage when a first minimum field strength of the magnetic field is exceeded, wherein the coil device has a coil core or a core element having a magnetization which varies abruptly depending on the acting magnetic field strength or having a layer arrangement of soft and hard magnetic material.

19. The electrode device according to claim 14, wherein the electrode device comprises a coil device, wherein an electrical impulse having a voltage of at least 0.5 V and a time duration of at least 0.05 ms can be generated by the coil device by at least one of an external and a varying magnetic field having a field strength in the region of the electrode device of at most 10 mT.

20. The electrode device according to claim 14, wherein the electrode device preferably comprises at least one of a passively operating pulse forming device, in particular having at least one of an inductance, a capacitance and a resistance;
the electrode device is configured as at least one of a battery-less and amplifier-less device; and
the electrode device comprises a coil device with a magnetic core, the core being magnetically soft or ultra-soft.

21. The electrode device according to claim 14, wherein the electrode device is configured such that each pulse-like induction voltage is output as an electrical impulse.

22. The electrode device according to claim 14, wherein the frequency of the magnetic field is less than 3 Hz or corresponds to the desired frequency of the electrical impulses to be generated.

23. The electrode device according to claim 14, wherein the electrode device is configured in such a manner that it generates and delivers an electrical impulse each time the minimum field strength is exceeded.

24. The electrode device according to claim 14 wherein the electrode device is a cardiac pacemaker.

25. The electrode device according to claim 14 wherein the electrode device comprises only passive components and a rectifier.

26. The electrode device according to claim 14, wherein the electrode device comprises a coil device, wherein the coil device comprises at least 1,000 turns.

27. A method comprising: operating an implantable electrode device for generating electrical impulses, wherein the electrode device is supplied with energy and directly controlled by means of a magnetic field to generate the electrical impulses, wherein the magnetic field in a switched-on state is formed by a plurality of unipolar or bipolar magnetic field pulses and that a respective switch-on time of the magnetic field controls or determines the length of the electrical impulse respectively generated by the electrode device or during a contiguous sequence of electrical impulses, wherein the number of magnetic field impulses is varied for a variation of the duration of each electrical impulse or a contiguous sequence of electrical impulses or wherein the magnetic impulses have a substantially sawtooth-shaped profile.

28. The method according to claim 27, wherein the magnetic field has a switch-on ratio of less than 0.5 or less than 0.25 or substantially 0.1 or less.

29. The method according to claim 27, wherein the magnetic field is at least one of generated intermittently and has a switch-on ratio of less than 0.5 or less than 0.25 or substantially 0.1 or less.

30. The method according to claim 27, wherein the magnetic field is alternately generated with an opposite field direction for the alternate generation of an electrical impulse and the electrode device is activated before generating the next electrical impulse, in particular wherein the activation takes place shortly before generation of the next electrical impulse.

31. The method according to claim 30, wherein the activation takes place shortly before generation of the next electrical impulse.

32. The method according to claim 30, wherein an electrical impulse is generated and delivered each time the minimum field strength is exceeded.

33. The method according to claim 27, wherein the frequency of the magnetic field is less than 3 Hz or corresponds to the desired frequency of the electrical impulses to be generated.

34. The method according to claim 27, wherein at least one of:
in the switched-on state the magnetic field is formed by a plurality of unipolar or bipolar magnetic field pulses;
a respective switch-on duration of the magnetic field controls or determines the length of each electrical impulse of a stimulation generated by the electrode device; and
the magnetic field is utilized for energy recovery.

35. The method according to claim 27, wherein the field strength of the magnetic field in the region of the electrode device is substantially 1 to 20 mT, in particular 2 to 10 mT.

36. The method according to claim 27, wherein an electrical impulse is only generated when a first minimum field strength of the magnetic field is exceeded.

37. The method according to claim 27, wherein an electrical impulse can be generated in each case only following previous activation by exceeding a second minimum field strength of the magnetic field having the opposite field direction to the field direction for the generation of an electrical impulse.

38. The method according to claim 27, wherein an electrical impulse can be generated in each case only following previous activation by exceeding a second minimum field strength of the magnetic field, wherein the second minimum field strength is greater than the first minimum field strength; or
wherein the minimum field strength is substantially 0.5 to 20 mT.

39. The method according to claim 27, wherein a pulse-like induction voltage is generated when a first minimum field strength of the magnetic field is exceeded wherein the coil device comprises at least one of a coil core or a core element having a magnetization which varies abruptly depending on the acting magnetic field strength and a wire-like layer arrangement of soft and hard magnetic material.

40. The method according to claim 27, wherein a pulse-like induction voltage is generated when a first minimum field strength of the magnetic field is exceeded; and wherein each pulse-like induction voltage is output as an electrical impulse.

41. The method according to claim 27, wherein the electrode device comprises a coil device, wherein an electrical impulse having a voltage of at least 0.5 V and a time duration of at least 0.05 ms can be generated by the coil device by at least one of an external and a varying magnetic field having a field strength in the region of the electrode device of at most 10 mT.

42. The method according to claim 27, wherein the electrode device is a cardiac pacemaker.

43. The method according to claim 27, wherein the electrode device comprises a coil device comprising at least 1,000 turns.

44. A method comprising: operating an implantable electrode device for generating electrical impulses, wherein the electrode device is supplied with energy and directly controlled by means of a magnetic field to generate the electrical impulses, wherein the magnetic field in a switched-on state is foamed by a plurality of unipolar or bipolar magnetic field pulses and that a respective switch-on time of the magnetic field controls or determines the length of the electrical impulse respectively generated by the electrode device or during a contiguous sequence of electrical impulses,
wherein the field strength of the magnetic field, at least during switch-on times, has a substantially ramp- or sawtooth-shaped time profile.

45. The method according to claim 44, wherein the electrode device is a cardiac pacemaker.

46. The method according to claim 44, wherein the magnetic field has a switch-on ratio of less than 0.5.

47. The method according to claim 44, wherein at least one of the magnetic field is generated intermittently, and the magnetic field has a switch-on ratio of:
less than 0.5;
less than 0.25; or
approximately 0.1 or less.

48. The method according to claim 44, wherein the magnetic field is alternately generated with an opposite field direction for the alternate generation of an electrical impulse and the electrode device is activated before generating the next electrical impulse, in particular wherein the activation takes place shortly before generation of the next electrical impulse.

49. The method according to claim 44, wherein the frequency of the magnetic field is less than 3 Hz, and in particular corresponds to the desired frequency of the electrical impulses to be generated.

50. The method according to claim 44, wherein at least one of in the switched-on state the magnetic field is formed by a plurality of unipolar or bipolar magnetic field pulses, the respective switch-on duration of the magnetic field controls or determines the length of each electrical impulse of a stimulation generated by the electrode device, and the magnetic field is utilized for energy recovery.

51. The method according to claim 44, wherein the field strength of the magnetic field in the region of the electrode device is substantially 1 to 20 mT, in particular 2 to 10 mT.

52. The method according to claim 44, wherein an electrical impulse is only generated when a first minimum field strength of the magnetic field is exceeded, preferably wherein an electrical impulse is generated and delivered each time the minimum field strength is exceeded, preferably only after a respective preceding activation.

53. The method according to claim 44, wherein an electrical impulse can be generated in each case only following previous activation, in particular by exceeding a second minimum field strength of the magnetic field having the opposite field direction to the field direction for the generation of an electrical impulse, in particular wherein the second minimum field strength is greater than the first minimum field strength.

54. The method according to claim 44, wherein a pulse-like induction voltage is generated when a first minimum field strength of the magnetic field is exceeded, in particular wherein the coil device has a coil core or a core element comprises at least one of a magnetization which varies abruptly depending on the acting magnetic field strength and a wire-like layer arrangement of soft and hard magnetic material.

55. The method according to claim 44, wherein the electrode device comprises a coil device, wherein an electrical impulse having a voltage of at least 0.5 V and a time duration of at least 0.05 ms can be generated by the coil device by at least one of an external and varying magnetic field having a field strength in the region of the electrode device of at most 10 mT, in particular substantially 2 mT or less and wherein the coil device comprises at least 1,000 turns.

56. The method according to claim 44, wherein an electrical impulse can be generated in each case only following previous activation by exceeding a second minimum field strength of the magnetic field having the opposite field direction to the field direction for the generation of an electrical impulse wherein the second minimum field strength is greater than the first minimum field strength or wherein the minimum field strength is substantially 0.5 to 20 mT.

57. The method according to claim 44, wherein a pulse-like induction voltage is generated when a first minimum field strength of the magnetic field is exceeded; and wherein each pulse-like induction voltage is output as an electrical impulse.

* * * * *